United States Patent [19]

Fuson

[11] 3,987,930

[45] Oct. 26, 1976

[54] DUAL-ENDED TUBING CAP

[75] Inventor: Robert Lee Fuson, North Branch, N.J.

[73] Assignee: Ethicon, Inc., Somerville, N.J.

[22] Filed: Sept. 26, 1974

[21] Appl. No.: 509,362

[52] U.S. Cl. .......................... 220/352; 128/214 R; 128/272; 138/96 R; 138/89; 206/508; 206/509; 220/356; 220/380

[51] Int. Cl.² .................. A61M 1/00; A61M 25/00; B65D 41/28

[58] Field of Search ........... 220/258, 352, 356, 380; 206/503, 508, 509, 510, 499; 138/89, 96 R, 89.3; 128/2 F, 272, 348, 349 R, 350 R, DIG. 5, 214 R

[56] References Cited
UNITED STATES PATENTS

| | | | |
|---|---|---|---|
| 1,710,363 | 4/1929 | Kramer | 220/352 |
| 2,031,312 | 2/1936 | Horlick | 220/356 |
| 2,295,688 | 9/1942 | Reinhardt | 220/258 |
| 2,780,243 | 2/1957 | Williams | 206/515 |
| 2,801,020 | 7/1957 | Leake | 220/356 |
| 2,848,999 | 8/1958 | McGrew | 128/DIG. 5 |
| 3,030,955 | 4/1962 | Gossett | 128/272 |
| 3,104,681 | 9/1963 | Gray | 138/96 R |
| 3,307,552 | 3/1967 | Strawn | 128/348 |
| 3,610,242 | 10/1971 | Sheridan | 128/2 F |
| 3,835,862 | 9/1974 | Villari | 128/349 R |

*Primary Examiner*—George E. Lowrance
*Attorney, Agent, or Firm*—John J. Simkanich

[57] ABSTRACT

An intravenous tubing cap for sealing the end of a male tubing coupling or a female tubing coupling is provided by a plug having a tapered male fitting at one end being backed against a tapered female fitting at the other end. The plug may be molded in one piece with the back of the male portion forming a contiguous part of the female portion. Preferably, a serrated protective skirt around the male fitting provides a surface by which the cap may be grasped.

4 Claims, 5 Drawing Figures

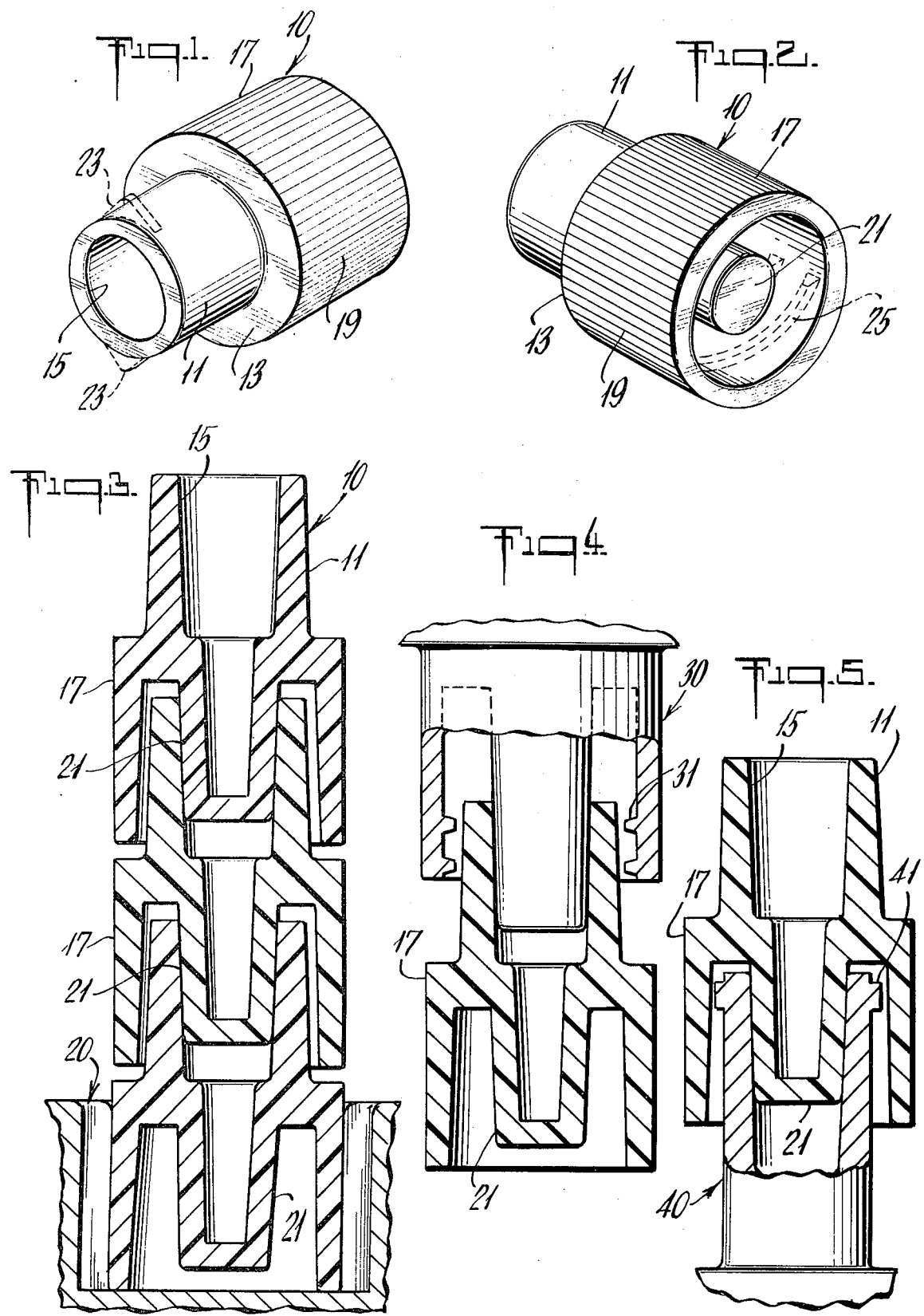

DUAL-ENDED TUBING CAP

BACKGROUND OF THE INVENTION

In many phases of medical practice, including use in the operating room and the treatment room, intravenous tubing is an important part of medical treatment apparatus. Most often tubing connections are not permanent but must be made, broken and remade according to the usage of the equipment. During these construction phases, the sterility of tubing must be maintained.

Intravenous tubing connections are most often made utilizing the medical industry's standardized Luer taper fittings. These fittings, which may either be male couplings or female couplings, include a tapered end of standardized dimensions. Coupling is made by the press-fit of mating parts.

Tubing caps are often used to seal the ends of unused or unnecessary tubing. These caps protect the sterility of the tubing and prevent fluid loss and/or particulate contamination.

Intravenous tubing caps available in the prior art of which there are many, have been for a single purpose, that is, they have been either male fitting closures or female fitting closures. These caps invariably have had flat end sections which complete the closure, the seal being made by a pressure fit of the mating tapered surfaces. A threaded lock-fit may or may not also have been utilized. They have been made of plastic or rubber.

These prior art caps have several disadvantages which make them difficult to use and hard to keep track of in an operating room environment. These caps are hard to grasp, especially when wet, because of their smooth plastic bodies and because of their small size. Moreover, the supply of male caps verses the supply of female caps needed to service closure must constantly be monitored. Additionally, caps which are not in use are troublesome to manage. They easily bounce around, roll off of surfaces and fall to the floor.

It is desirable, therefore, to have a tube cap which is multifunctional or dual purpose. It is also desirable that this cap be easy to work with and that it be easy to store. It is, moreover, desirable to lower inventory costs and inventory management problems.

An objective of this invention, therefore, is to provide a dual purpose, male-female closure cap, for any product having Luer taper intravenous fittings.

Another objective of this invention is to provide a cap which is easily grasped even when wet.

A further objective of this invention is to provide a cap which can easily be stored by stacking.

Another objective is to provide a method of storing unused caps.

An even further objective is to provide a cap with which a cost reduction in production and inventory may be obtained.

SUMMARY OF THE INVENTION

The objectives of this invention are provided by a dual-ended tubing cap for plugging a male or a female Luer-taper tube fitting. A Luer-tapered plug portion may be surrounded for its entire length by a cylindrical skirt having a serrated outer surface. The skirt may be circumferentially positioned a sufficient distance from the male plug to allow clearance for flanged lock-fittings present on some tubing couplings.

A Luer-tapered female plug may abut the skirted male portion, in back to back fashion, to form a cap having the female plug on one end and the male plug on the other end. The outside diameter of the female plug portion is preferably less than the inside diameter of the male plug protective skirt.

The entire cap may be injection molded as a single piece of polyethelene plastic.

Caps may be stored by stacking one upon another, in tandom fashion, by mating respective male and female portions. A stack of caps may be stored by placing one end of the stack in a receptacle socket. When stored in this manner, caps are ready for use when removed from the stack one at a time.

DESCRIPTION OF THE DRAWINGS

The features of this invention can be easily understood from the following detailed description and the appended claim, read in conjunction with the following drawings, in which like numerals refer to like parts and in which:

FIG. 1 is a perspective view of the female end of the cap.

FIG. 2 is a perspective view of the male end of the cap.

FIG. 3 is a longitudinal cross section of a stack of the subject caps in a receptacle socket.

FIG. 4 is a longitudinal cross section of the subject cap mating a female tubing fitting.

FIG. 5 is a longitudinal cross section of the subject cap mating a male tubing fitting.

DETAILED DESCRIPTION OF THE INVENTION

A dual purpose intravenous tubing cap is provided for sealing both male and female Luer-tapered intravenous tubing end fittings.

FIG. 1 is a perspective view of the female plugging portion of the cap 10. A cylindrical structure 11 extends from a back surface 13 and has a concentrically-positioned, longitudinal Luer tapered-bore 15. This cylinder 11 has a constant outside diameter and a bore 15 which is reduced in diameter at an angle of one-degree, forty-five minutes going into the cylinder 11. The end of the cylinder 11 has been parted-off to be perpendicular with the longitudinal axis of the bore 15. The back plate 13 is circularly shaped and is situated to have the same centerline axis as the cylinder 11 and the bore 15.

Extending about the longitudinal centerline-axis of the cap, which axis being referred to above, and away from the female plugging cylinder 11 and beginning at the back plates 13, is a cylindrically shaped skirt, FIG. 2. The skirt 17 has a large cylindrical center bore of a dimension larger than the outside diameter of cylinder 11. Serrations 19 are longitudinally cut into the outer surface of this skirt 17. The end of the skirt 17 is parted off perpendicular to its longitudinal center line.

A concentrically-positioned, male, Luer-tapered cylindrical plug 21 extends out of the back plate 13 away from the cylinder 11 and concentrically within the protective skirt 17, to a point short of the end of the skirt 17. This plug 21 tapers down at an angle of 1°, 45 min. from the back plate 13 to its free end, this free end being perpendicular to the extension of the plug 21.

Luer-tapered plugs, both male and female as stated above have a taper angle of one-degree, forty-five minutes. The outside diameter of the plug and the length of the plug are also defined within specified tolerances.

Thus, the dimensions of the instant invention may be varied from those to be given below without departing from the scope or application of the invention.

A stack of three caps 10 inserted within and extending out of a receptacle 20 are shown in sectional view in FIG. 3. As seen from the FIG. 3, these caps 10 may be stacked together, end to end, with the male end of a succeeding cap mating with the female end of a proceeding cap. A plurality of caps 10 may be easily stored and handled while stacked. These caps may be injection molded as a single piece of polyethelene plastic. The cylinder 11 is 0.280+0.005 inches long and has a 0.265 inch diameter. The tapered bore 15 of cylinder 11 extends to its full depth at a taper of 1°45' from an outer diameter of 0.163+0.004 inches. The cylinder 11 has a nominal wall thickness of 0.045 inches. The back plate 13 has an outer diameter of 0.385+.002 inches and a thickness of 0.55+0.60 inches. A hole may exist through the center of the back plate 13 as a result of the injection molding process. This hole continues through the plate 13 to almost the end of the plug 21 to render the plug hollow and having a uniform wall thickness on its side and end walls. The skirt 17 can be 0.280+0.005 inches long with an outer diameter dimension of 0.385+0.002 inches and an inner diameter of 0.315+0.003 inches. The nominal wall thickness of the skirt 17 is 0.035 inches. The serrations 19 are 0.015 inches deep around a 0.385 inch outer diameter. The tapered male plug 21 is 0.245+0.005 inches long and has a 1°45' taper from an outer diameter of 0.153+0.002 inches. The male plug 21 has a nominal wall thickness of 0.04 inches.

FIG. 4 shows a sectional of the female portion of the cap 10 mating and sealing off a male tubing coupling 30 via a pressure or friction fit or lock along the tapered mating surfaces. The dimensions of the cap 10 are such so as to clear any threads 31 which may protrude from the coupling 30. In an alternate embodiment, the cap 10 may have a pair of protruding flanges 23 FIG. 1., which would engage these threads 31, FIG. 4, providing a positive lock. The flanges 23 may comprise a pair of triangularly shaped sections 23 (FIG. 1) positioned diametrically opposed on the outside diameter of the cylinder 11 near its free end away from back plate 13.

A sectional view of the male portion of the cap 10, mating and sealing off a female tubing coupling 40 via a pressure fit is shown in FIG. 5. The dimensions of the skirt 17 portion of the cap 10 are such that protruding flanges 41 present on the end of the coupling 40 is not engaged. In the alternate embodiment mentioned above, the skirt 17 of the cap 10 would have screw threads 25, FIG. 1, extending toward the plug 21 from the inner surface of the skirt for engaging the flanges 41 or the flanges 23 and for providing a positive screw lock in addition to the pressure fit or lock.

A single dual purpose cap 10, is therefore, available for sealing off or capping off the ends of either male or female tubing couplings to stop the flow of fluids and to seal against contamination. The utilization of this cap permits a cost reduction to the user, in that the injection molded dual-ended cap 10 costs about as much as one of the prior art single purpose male caps or female caps. The user can additionally realize a reduction in inventory and handling costs by storing a single dual-ended cap where before he stored two single ended caps. Moreover, there is an increased efficiency in use by medical personnel.

The above description is to be taken as illustrative and not in the limiting sense. Many modifications may be made to the design without deviating from the scope thereof.

What is claimed is:
1. A cap for sealing Luer-tapered intravenous tubing couplings, comprising:
   means for capping off a male Luer-tapered tubing end having a Luer-tapered surface; and
   means for capping off a female Luer-tapered tubing end having a Luer-tapered surface and being connected to and protruding from said male end capping off means;
   said male end capping off means including a back plate with a cylindrical structure extending therefrom, said cylindrical structure having a constant outside diameter, a tapered bore which is reduced going into said cylinder and an end parted off perpendicular to the longitudinal axis of said bore;
   said female end capping off means including a tapered plug extending from said back plate and tapering down to a free end being perpendicular to the extension of said plug, and a cylindrical skirt extending from said back plate about said tapered plug;
   said cylindrical structure, said tapered bore, said tapered plug and said cylindrical skirt having a same centerline axis and being of dimensional sizes to permit stacking, male-end-to-female-end, and female-end-to-male-end, of said cap with identical caps.
2. The cap of claim 1 also including:
   a pair of triangularly shaped flange sections being positioned diametrically opposed on the outside diameter of said cylinder near said cylinder free end; and
   screw threads extending from the inner surface of said cylindrical skirt.
3. The cap of claim 2 wherein said tapered plug is hollow, having uniform side and end wall thickness and wherein said hollow plug is formed by the continuation of a hole through said back plate to almost the end of said tapered plug.
4. The cap of claim 3 wherein said cylindrical structure, said tapered plug and said cylindrical skirt are made out of a single piece of injection molded plastic.

* * * * *